US010472687B2

(12) United States Patent
Peterson et al.

(10) Patent No.: US 10,472,687 B2
(45) Date of Patent: Nov. 12, 2019

(54) METHODS TO IDENTIFY ANTITUBERCULOSIS COMPOUNDS

(71) Applicant: Institute for Systems Biology, Seattle, WA (US)

(72) Inventors: Eliza Peterson, Seattle, WA (US); Nitin S. Baliga, Seattle, WA (US)

(73) Assignees: Institute for Systems Biology, Seattle, WA (US); Center for Infectious Disease Research, Seattle, WA (US)

( * ) Notice: Subject to any disclaimer, the term of this patent is extended or adjusted under 35 U.S.C. 154(b) by 0 days.

(21) Appl. No.: 16/068,670

(22) PCT Filed: Jan. 6, 2017

(86) PCT No.: PCT/US2017/012616
§ 371 (c)(1),
(2) Date: Jul. 7, 2018

(87) PCT Pub. No.: WO2017/120529
PCT Pub. Date: Jul. 13, 2017

(65) Prior Publication Data
US 2019/0032157 A1      Jan. 31, 2019

Related U.S. Application Data

(60) Provisional application No. 62/276,682, filed on Jan. 8, 2016.

(51) Int. Cl.
*C12Q 1/6897* (2018.01)
*C12Q 1/689* (2018.01)

(52) U.S. Cl.
CPC .......... *C12Q 1/6897* (2013.01); *C12Q 1/689* (2013.01); *C12Q 2600/106* (2013.01); *C12Q 2600/136* (2013.01); *C12Q 2600/156* (2013.01); *C12Q 2600/158* (2013.01); *G01N 2333/4703* (2013.01); *G01N 2800/12* (2013.01)

(58) Field of Classification Search
None
See application file for complete search history.

(56) References Cited

U.S. PATENT DOCUMENTS

| | | |
|---|---|---|
| 7,075,582 B2 | 7/2006 | Alekshun et al. |
| 2011/0190199 A1 | 8/2011 | Brickner et al. |

FOREIGN PATENT DOCUMENTS

| | | |
|---|---|---|
| WO | WO 2004/041209 | 5/2004 |
| WO | WO 2015/107482 | 7/2015 |

OTHER PUBLICATIONS

Hartkoorn et al. Antimicro. Ag. and Chemo., 58, 5, 2979-2981 (Year: 2014).*
Campen et al., Tuberculosis, 95, 4, 432-439, (Year: 2015).*
Andries et al., "A diarylquinoline drug active on the ATP synthase of *Mycobacterium tuberculosis*," Science (2005) 307(5707):223-227.
Berney et al., "A *Mycobacterium tuberculosis* Cytochrome bd Oxidase Mutant is Hypersensitive to Bedaquiline," mBio (2014) 5:e01275-01214.
Campen et al., "Development of a *Mycobacterium smegmatis* transposon mutant array for characterizing the mechanism of action of tuberculosis drugs: Findings with isoniazid and its structural analogues," *Tuberculosis* (2015) 95(4):432-439.
Chatterji et al., "1,4-Azaindole, a Potential Drug Candidate for Treatment of Tuberculosis," Antimicrob Agents Chemother (2014) 58(9):5325-5331.
Dhillon et al., "Bactericidal activity of the diarylquinoline TMC207 against *Mycobacterium tuberculosis* outside and within cells," *Tuberculosis* (2010) 90(5):301-305.
Eldholm et al., "Evolution of extensively drug-resistant *Mycobacterium tuberculosis* from a susceptible ancestor in a single patient," Genome Biology (2014) 15:490.
Gao et al., "Structure of the MarR family protein Rv0880 from *Mycobacterium tuberculosis*," Acta Crystallogr F Struct Biol Commun (2015) 71(Pt 6):741-745.
Hartkoorn et al., "Cross-resistance between clofazimine and Bedaquiline through upregulation of MmpL5 in *Mycobacterium tuberculosis*," Antimicrobial Agents and Chemotherapy (2014) 58(5):2979-2981.
Hopkins, "Network pharmacology," Nat Biotechnol (2007) 25(10):1110-1111.
Korcsmaros et al., "How to design multi-target drugs," Expert Opin on Drug Discovery (2007) 2:799-808.
Koul et al., "Delayed bactericidal response of *Mycobacterium tuberculosis* to bedaquiline involves remodelling of bacterial metabolism," Nature Communications (2014) 5:3369.
Peterson et al., "Network analysis identifies Rv0324 and Rv0880 as regulators of bedaquiline tolerance in *Mycobacterium tuberculosis*," Nature Microbiology (2016) 1(8):16078.
Phillips, "Infectious disease: TB's revenge," Nature (2013) 493(7430):14-16.
Schubert et al., "The Mtb proteome library: A resource of assays to quantify the complete proteome of *Mycobacterium tuberculosis*," Cell Host & Mircobe (2013) 13(5):602-612.
Turkarslan et al., "A comprehensive map of genome-wide gene regulation in *Mycobacterium tuberculosis*," Scientific Data (2015) 2:150010.
World Health Organization, "Global Tuberculosis Report," (2012) 98 pages.

* cited by examiner

*Primary Examiner* — Nancy A Treptow
(74) *Attorney, Agent, or Firm* — Morrison & Foerster LLP

(57) ABSTRACT

Practical assays to identify compounds that overcome the resistance of *M. tuberculosis* to bedaquiline are based on transcription factors Rv0324 and Rv0880 shown to mediate this resistance.

4 Claims, 3 Drawing Sheets

METHODS TO IDENTIFY ANTITUBERCULOSIS COMPOUNDS

CROSS-REFERENCE TO RELATED APPLICATIONS

This application is the national phase of PCT application PCT/US2017/012616 having an international filing date of 6 Jan. 2017, which claims benefit of U.S. Provisional Application No. 62/276,682, filed 8 Jan. 2016. The contents of the above patent applications are incorporated by reference herein in their entirety.

STATEMENT OF RIGHTS TO INVENTIONS MADE UNDER FEDERALLY SPONSORED RESEARCH

This work was supported in part by a U.S. government grant and the U.S. government has certain rights in this invention.

TECHNICAL FIELD

The invention is in the field of assay methods to identify compounds useful in treating tuberculosis. More particularly, it is directed to methods to identify compounds that can potentiate the effectiveness of the known antitubercular compound bedaquiline (BDQ). The invention takes advantage of evaluating networks of transcriptional regulation.

BACKGROUND ART

Tuberculosis (TB) continues to be one of the greatest infectious disease threats to human health. The emergence of multidrug-resistant (MDR) and extensively drug-resistant (XDR) strains of *Mycobacterium tuberculosis* (MTB) further complicate the control of TB (Phillips, L., *Nature* (2013) 493:14-16, WHO. Global Tuberculosis Report (2012)). To confront these challenges, more effective TB therapies must be developed. Current drug discovery efforts have yielded few new antitubercular drug treatments. In particular, a major challenge lies in understanding the systems-scale consequences that result from perturbing MTB with a drug (Korcsmaros, T., et al., *Expert Opin. on Drug Discovery* (2007) 2:799-808). It has recently been appreciated that the interconnectivity of biological networks can provide robustness to drug treatment and a tendency to minimize drug impact (Eldholm, V., et al., *Genome Biol.* (2014) 15:490, Koul, A., et al., *Nat. Commun.* (2014) 5:3369).

There are now a number of examples of registered drugs that hit specific targets very well but show lower efficacy than expected in vivo due to compensatory responses (Hopkins, A. L., *Nat. Biotech.* (2007) 25:1110-1111). In particular, the antitubercular drug, bedaquiline (BDQ) received FDA approval in 2012 and has high selectivity for mycobacterial $F_1F_o$ ATP synthase, but displays almost no bactericidal activity during the first 4-6 days (Andries, K., et al., *Science* (2005) 307:223-227, Dhillon, J., et al., *Tuberculosis* (2010) 90:301-305 and Berney, M., et al., *mBio* (2014) 5:e01275-01214). Transient MTB tolerance, mediated by regulatory control, could be responsible for the delayed onset of killing by BDQ, and a better understanding of the regulatory mechanisms that effect transition to the tolerant state in response to BDQ should reveal novel hypotheses to improve therapeutic outcomes.

Although the theoretical basis is not entirely clear, it is common for tuberculosis treatment to involve combinations of drugs. For example, US2011/0190199 describes a particular compound which can be used in combination with two other agents that are combined with it and among those that are candidates are PA-824 and BDQ. Similarly, WO2015/107482 describes combinations of the compound of that application with three antitubercular agents which are selected from a list that includes PA-824 and BDQ. In addition, Chatterjee, M., et al., *Antimicrob. Agents Chemother.* (2014) 58:5325-5331 shows synergy of the compound described therein with PA-824 and BDQ in vitro. Numerous such combinations are known in the art.

It has now been shown that certain transcription factors are responsible for a BDQ-specific tolerant state and by testing the ability of candidate drugs to modulate the activity of these transcription factors, drugs can be identified that will overcome the tolerant state and potentiate the activity of BDQ. By identifying regulatory factors that are associated with the tolerance exhibited by MTB to BDQ, convenient assays have been developed to identify compounds that will potentiate the bactericidal activity of BDQ.

DISCLOSURE OF THE INVENTION

Applicants have found that two specific transcription factors, Rv0324 and Rv0880 are relevant to the development of BDQ resistance. Therefore, in one aspect, the invention is directed to a method to identify companion compounds to potentiate BDQ by assessing their ability to affect the activity of transcription factor Rv0880 or of transcription factor Rv0324.

In another aspect, the invention is directed to a method to identify a drug useful in combination with BDQ, which method comprises determining the transcriptome of MTB that has been treated with a candidate drug and comparing said transcriptome to the transcriptome of a mutant of MTB that is constitutively tolerant to BDQ, whereby a candidate drug that generates a transcriptome similar to that of said mutant is identified as a drug useful in combination with BDQ.

BRIEF DESCRIPTION OF THE DRAWINGS

FIG. 1A shows the results over a seven day period; FIG. 1B shows the same results on a log scale but normalized to growth in the absence of bedaquiline and FIG. 1C compares the overall growth trajectories of the three strains in the presence of bedaquiline.

MODES OF CARRYING OUT THE INVENTION

Figure 1:
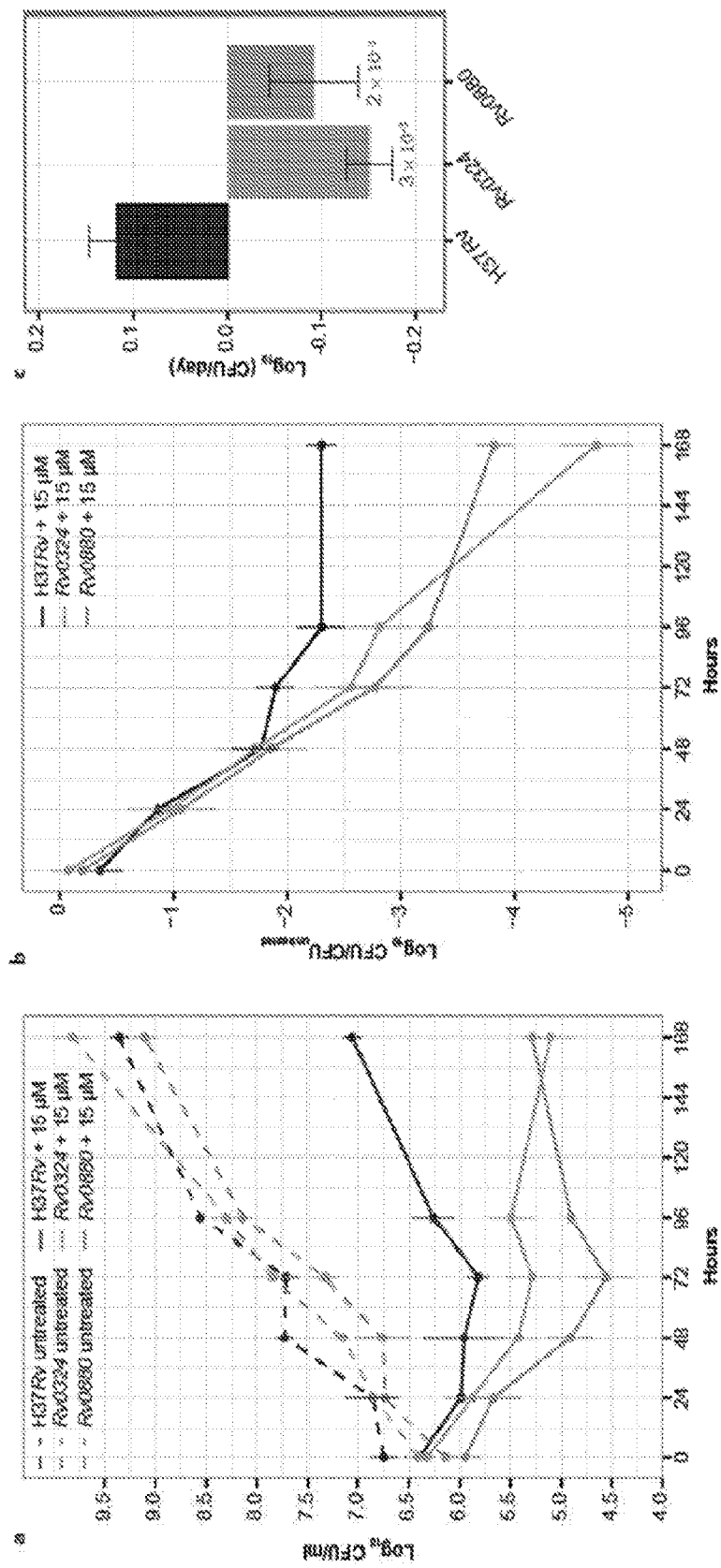
FIGS. 1A-1C show the results of treatment with 15 μM bedaquiline on the growth rate of wildtype MTB as compared to knockout strains lacking Rv0324 or Rv0880.

During the first 96 hours after BDQ treatment of MTB, little bactericidal activity is shown even at 30 times the minimal inhibitory concentration (MIC). Koul, A., et al., *Nat. Commun.* (2014) supra. However, after 96 hours, effective MTB killing occurs. Based on this, genome-wide gene expression data were determined at 48 and 96 hours. Gene expression at 48 and 96 hours clustered tightly in principal component analysis and were combined for further analysis. Based on the gene expression data, it was found that after BDQ treatment at 15 µM concentration, 1,121 genes significantly differentially express as compared to untreated samples, using a moderated t-test ($-1 \leq \log_2$ fold-change$\leq$and Benjamini-Hochberg, BH, multiple hypothesis adjusted P-value<0.01). Of the 1,121 differentially expressed genes, a large majority (897 out of 1,121) were downregulated and there was an overall gene enrichment for the TubercuList category, (Lew, J. M., et al., *Tuberculosis* (2011) 91:1-7, doi:10.1016/j.tube.2010.09.008) 'information pathways' (BH adjusted P-value=$8.9 \times 10^{-4}$). Similarly, 86 of the 89 differentially expressed genes associated with the 'information pathway' TubercuList category were downregulated and include many components of the large and small ribosomal subunits. This suggests a pronounced downregulation of protein synthesis occurs in the bedaquiline-resistant state.

The 1,121 differentially expressed genes were integrated with MTB EGRIN models described in Peterson, E. J., et al., *Nucleic Acids Res.* (2014) 42:11291-11303, doi:10-1093/nar/gku777; Turkarslan, S., et al., *Sci. Data* (2015) 2:150010, doi:10.1038/sdata,2015.10; and Ma, S., et al., Accepted at *PLoS Comput. Biol.* (2015). Significant enrichment (BH adjusted P-value<0.01) in 13 unique modules of co-regulated genes was detected. Predicted transcription factors (TF) for these modules were identified and Rv0324 was thus identified. Rv0324, an ArsR-type TF, is predicted to regulate 4 modules significantly enriched in bedaquiline-specific genes (BH adjusted P-value<0.01). In the modules regulated by Rv0324, 22 out of the 23 target genes are upregulated in response to bedaquiline treatment. Rv0324 has a significant increase in expression (>1.5 absolute $\log_2$ fold-change and BH adjusted P-value<0.01) upon bedaquiline treatment. This suggests bedaquiline treatment leads to the upregulation of a number of Rv0324 target genes, which may play a part in promoting a bedaquiline-tolerant state. In addition, the genes of the Rv0324 bedaquiline-resistance regulon are significantly enriched in the TubercuList category, 'virulence, detoxification, and adaptation' (BH adjusted P-value=$3.5 \times 10^{-8}$). Many of the Rv0324 target genes that belong to this category are part of the cell wall-localized mce3 operon. While the exact role of the mce3 operon is unknown, it is generally associated with virulence and resistance to antimicrobial mechanisms.

A bedaquiline-specific PROM model was constructed by overlaying the bedaquiline treated transcriptome data using the iMAT approach. Shlomi, T., et al., *Nat. Biotechnol.* (2008) 1003-1010, doi:10.1038/nbt.1487; Zur, H., et al., *Bioinf.* (2010) 3140-3142, doi:10.1093/bioinformatics/btq602 (2010). The resulting iMAT-PROM model represents the metabolic state of MTB when exposed to bedaquiline and was used to simulate the phenotypic outcome of 104 TF knockout events. These simulations identified Rv0880 as yielding a strong defect when knocked out in the presence of bedaquiline, but not in its absence. Rv0880 under standard culture conditions, modulates the expression of 23 genes, 17 of which were significantly differentially expressed when treated with bedaquiline. The Rv0880 bedaquiline-response regulon also contains a notable number of upregulated genes (8 out of 17). Nonetheless, Rv0880 has a significant decrease in expression (>2.0 absolute $\log_2$ fold-change and BH adjusted P-value<0.01) after 48-96 hours of bedaquiline treatment. Presumably, the bedaquiline-induced repression of Rv0880 leads to mixed expression changes of its regulatory targets. The regulatory targets of Rv0880 are enriched in the TubercuList category, 'cell wall and cell processes' (BH adjusted P-value=$1.9 \times 10^{-3}$), which could contribute to a bedaquiline-tolerant state in complex ways.

The method of the invention employs MTB strains that carry a reporter gene fused to a promoter that specifically responds to a treatment with the antitubercular drug, BDQ. To develop this assay, a regulatory network model constructed for MTB (Peterson, E. J., et al., *Nucleic Acids Res.* (2015) 42:11291-11303) was employed. The results are described in Peterson, E. J., et al., *Nat. Microbiol.* (submitted). Subnetworks were identified that push MTB into an adaptive tolerant state in response to bedaquiline treatment. Perturbation of transcription factors, Rv0324 and Rv0880, key regulators of the adaptive tolerant state, results in significantly increased bedaquiline killing. Further, systems analysis predicts that the activity of transcription factor, Rv0324, may be controlled by the level of nutrients (i.e., fatty acids) contained in macrophages, and that MTB residing in macrophages abundant in fatty acids may not alter their tolerance to BDQ.

In one embodiment, the invention is directed to an assay wherein a reporter gene is fused to promoters of specific Rv0324 or Rv0880 regulatory targets and screening for compounds that inhibit the enhanced expression of the reporter. Details are set forth in Example 1.

An alternate approach compares transcriptomes induced by a candidate drug to the transcriptome of mutants of MTB that are constitutively tolerant to BDQ. Using this approach and testing 36 compounds, pretomanid (PA-824) was identified. PA-824 is known to repress Rv0880 and has been used in combination with BDQ in protocols involving at least a thiol drug.

The following examples are offered to illustrate but not to limit the invention.

PREPARATION A

Effect of Rv0324 and Rv0880 Knockouts

Knockout strains of MTB H37Rv lacking either Rv0324 or Rv0880 were obtained according to the techniques described in Tufariello, J. M., et al., *mBio* (2014) 5:e01179-01114. These strains, along with wildtype were grown under standard conditions, but with the addition of 15 µM bedaquiline and colony forming units (CFU's) were monitored over seven days with the results shown in FIG. 1A. As shown, the wildtype strain was more resistant to bedaquiline treatment than either of the knockout strains. FIG. 1B shows the same results on a logarithmic scale and normalized to CFU's for untreated controls. The decrease in surviving cells caused by bedaquiline treatment was similar for wildtype and mutant strains over the first 48 hours, but after that, the Rv0324 knockout showed a 1.8 $\log_{10}$ greater survival deficiency and Rv0880 showed a 1.3-fold $\log_{10}$ greater survival deficiency compared to the wildtype by the endpoint of seven days (168 hours).

FIG. 1C shows that over the seven days of treatment, the wildtype strain had a positive growth rate at 15 µM bedaquiline concentration, but the mutant strains had negative overall growth. Similar results were obtained at 1.5 µM concentrations of bedaquiline, but to a lesser extent.

EXAMPLE 1

High Throughput Assay

GFP and RFP MTB Reporter Strains

Reporter strains of MTB that operably link fluorescent protein encoding nucleic acids to promoters known to be enhanced by the transcription factor Rv0324 were constructed in the MTB strain H37Rv. The relevant promoters are Rv3269c, Rv2323c, Rv1966 and Rv1936.

Regions containing ~500 bp immediately upstream of Rv3269c, Rv2323c, Rv1966 and Rv1936 were PCR amplified and placed in front of the nucleotide sequence encoding GFPmut3 in a modified replicating plasmid pSE100 (Abramovitch, R. B., et al., *Mol Microbiol* (2011) 80:678-694). These were transformed into H37Rv to obtain Rv3269'::GFP, Rv2323c'::GFP, Rv1966'::GFP, and Rv1936'::GFP. Similarly, Rv3269'::RFP, Rv2323c'::RFP, Rv1966'::RFP, and Rv1936'::RFP strains were constructed by fusing the same promoter regions to the mRFP gene.

Rv2323c'::GFP High Throughput Primary Screen

The fluorescence signal window between bedaquiline treated and un-treated was determined to be greatest for the Rv2323c'::GFP strain. Rv2323'::GFP starter culture was harvested at mid-log phase and diluted to an $OD_{600}$ of 0.2 in complete 7H9-GAT medium. The bacterial suspension was distributed into wells (30 μl/well) of a flat-bottom, dark, 384-well plate containing 10 μM of bedaquiline and 10 μM of test compound. Plates are incubated at 37° C. for 3 h and fluorescence signals (in relative fluorescence units [RFU]) measured with a microplate reader (excitation wavelength, 485 nm; emission wavelength, 520 nm) with a 90 s shaking prior to reading. Wells without bedaquiline were used as a positive control for screening hits. Hits are defined as compounds that reduce GFP signal response less than a threshold value defined by the mean minus twice the standard deviation and are retested in the primary screen assay.

Figure 2:
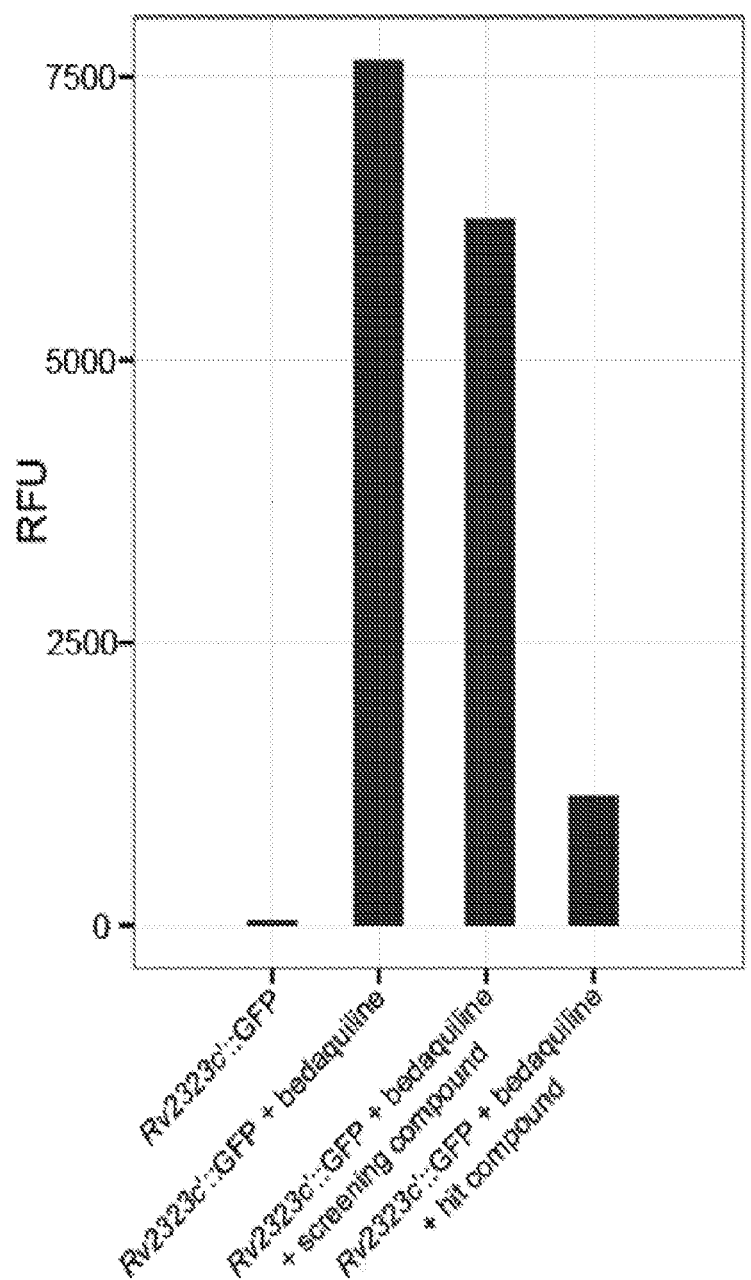
FIG. 2 is a graph showing the results of an assay wherein promoter of that responds to Rv0324, Rv2323c, is operatively linked to GFP. Low fluorescence signal levels are obtained in the absence of bedaquiline treatment, but in the presence of bedaquiline, the expression controlled by Rv2323c is induced by Rv0324 activity leading to increased fluorescence. High fluorescence levels remain when compounds that do not inhibit the regulatory activity of Rv0324 are added to MTB that contains this expression system but decrease below a statistical threshold when the MTB is treated with hit compounds.

FIG. 2 describes the results as shown. The strain itself generates little GFP in the absence of bedaquiline but in the presence of BDQ a high level of fluorescence is exhibited. Screened compounds that are not successful in overcoming BDQ only minimally diminish the fluorescence while hit compounds diminish it substantially.

Figure 3:
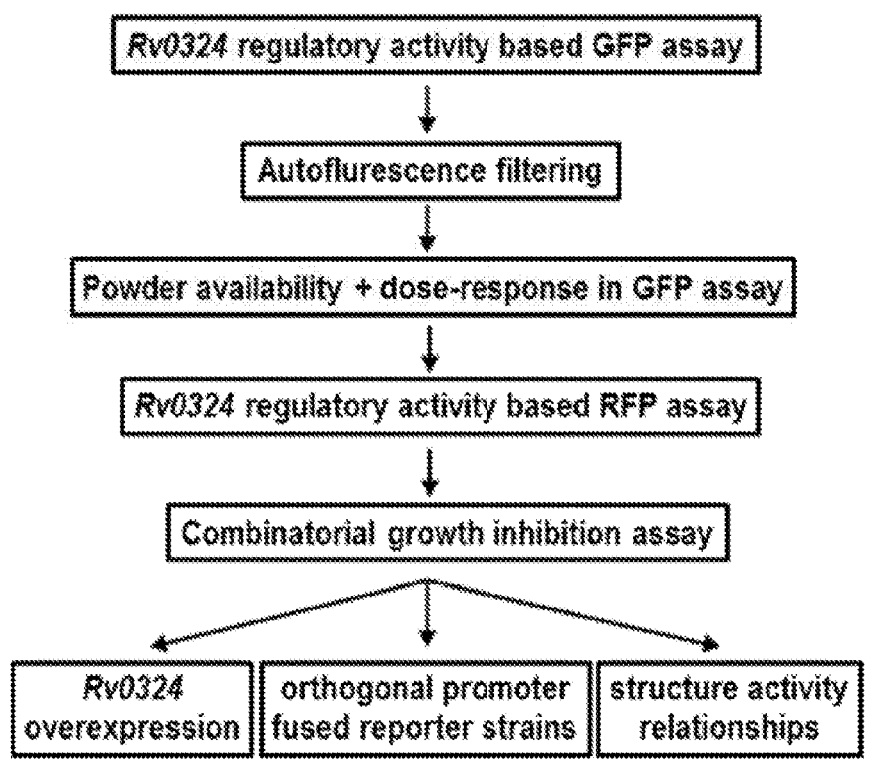
FIG. 3 shows a screening cascade and workup of hit compounds.

In order to verify the results of the initial assay, a screening protocol was devised as shown in FIG. 3. As shown, after correcting for autofluorescence, the successful compounds are tested for powder availability in a dose response GFP assay followed by a confirmatory assay based on expression of RFP.

Successful compounds are confirmed by MTB growth assays.

Autofluorescence Assay

Autofluorescence of retest-positive-hits is measured by dispensing each compound at 10 μM (in 90% DMSO) into a 384-well plate and measuring the fluorescence signal by using the same signal acquisition parameters as for the primary screen. Autofluorescent compounds were filtered out and remaining hits evaluated in dose-response in the GFP assay.

Rv2323c'::RFP Secondary Assay

Hits from the primary screen are subjected to secondary screening assays from fresh-powder stocks (90% DMSO) with Rv2323c' promoter fused to a mRFP gene (Rv2323c'::RFP). Hits are rescreened with Rv2323c'::RFP in the same procedure as the primary screen with GFP. Red fluorescence is acquired with excitation and emission wavelengths of 587 and 630 nm, respectively.

Combinatorial Growth Inhibition Activity

For the combinatorial drug exposure experiments, two concentrations of each bedaquiline and hit compounds (0.3× minimum inhibitory concentration (MIC) and 1×minimum inhibitory concentration (MIC) are tested in all four combined permutations:

0.3×MIC bedaquiline+0.3×MIC hit compound, 0.3×MIC bedaquiline+1×MIC hit compound, 1×MIC bedaquiline+0.3×MIC hit compound, 1×MIC bedaquiline+1×MIC hit compound).

These are compared with response to treating with bedaquiline alone, at the two concentrations (0.3×MIC and 1×MIC). For each dosing scheme, the drugs are supplemented into cultures of the wild type MTB H37Rv strain. Samples are taken for 7 days and plated onto 7H10 to assess colony forming units (CFUs).

Growth Inhibition Activity in Rv0324 Overexpressor

To determine whether the combinatorial growth inhibition effect of bedaquiline+hit compound is indeed due to interference with Rv0324 (and not some unrelated target), the effect of overexpressing Rv0324 on the growth inhibition activity of the hit compound is measured. To measure the growth consequences of overexpressing Rv0324, a strain MTB H37Rv(ATc::Rv0324) containing an anhydrotetracycline (ATc)-inducible expression vector of Rv0324, as described previously (Rustad, T. R., et al., *PLoS one* (2008) 3:e1502, doi:10.1371/journal.pone.0001502 and Rustad, T. R., et al., *Genome Biology* (2014) 15:502) was used. Using the same dosing scheme as the combinatorial growth inhibition assay, the drugs are supplemented into cultures of ATc:Rv0324 with and without ATc added. Samples are taken for 7 days and plated onto 7H10 to assess colony forming units (CFUs). Results wherein the overexpressing strain shows enhanced growth demonstrate that interference with Rv0324 is responsible for the desired activity of the hit compound.

Dose-Response Activity in Orthogonal Reporter Gene Fused Promoters

To further confirm the specificity of hit compounds, their dose-response activity in other MTB strains with GFP and RFP fused to the promoter of other Rv0324 regulatory targets that are differentially expressed during bedaquiline treatment are tested. The assays are performed in Rv3269'::GFP, Rv1966'::GFP, Rv1936'::GFP, Rv3269'::RFP, Rv1966'::RFP, and Rv1936'::RFP using the same procedure as described for Rv2323c'::GFP strain.

The invention claimed is:

1. A method to identify a compound that potentiates the treatment of tuberculosis (TB) by bedaquiline (BDQ) which method comprises assessing the ability of a test compound to diminish the activity of transcription factor Rv0880 or transcription factor Rv0324 wherein a compound that diminishes the activity of one or both of said transcription factors is identified as a compound that potentiates the treatment of tuberculosis with BDQ.

2. The method of claim 1 wherein said assessing is performed in a method that measures the effect of the test compound on the expression of a reporter gene operably linked to a promoter that is activated by said transcription factor.

3. The method of claim 2 wherein the reporter gene encodes a fluorescent protein.

4. The method of claim 3 which comprises:
(a) providing a strain of *M. tuberculosis* (MTB) that has been modified to contain an expression system wherein a nucleotide sequence encoding said fluorescent protein is operably linked to said promoter;
(b) treating a sample comprising said modified MTB with BDQ in the presence and absence of test compound;
(c) measuring the fluorescence of a test sample which comprises said test compound and measuring fluorescence of a control sample which does not contain said test compound; and
(d) comparing the level of fluorescence in the test sample as compared to the control sample
whereby a test compound that results in diminished fluorescence of the test sample as compared to the control sample is identified as a compound that potentiates the treatment of tuberculosis with BDQ.

* * * * *